US007785579B2

(12) United States Patent
Clark

(10) Patent No.: US 7,785,579 B2
(45) Date of Patent: Aug. 31, 2010

(54) MODIFIED TUMOR NECROSIS FACTOR

(75) Inventor: Mike A. Clark, Lexington, KY (US)

(73) Assignee: Polaris Group (CN)

( * ) Notice: Subject to any disclaimer, the term of this patent is extended or adjusted under 35 U.S.C. 154(b) by 98 days.

(21) Appl. No.: 11/363,863

(22) Filed: Feb. 27, 2006

(65) Prior Publication Data
US 2006/0222626 A1    Oct. 5, 2006

Related U.S. Application Data

(60) Division of application No. 09/504,280, filed on Feb. 15, 2000, now abandoned, which is a continuation-in-part of application No. 09/006,810, filed on Jan. 14, 1998, now abandoned.

(60) Provisional application No. 60/035,521, filed on Jan. 15, 1997.

(51) Int. Cl.
*A61K 38/19* (2006.01)
*C07K 14/525* (2006.01)

(52) U.S. Cl. .................. 424/85.1; 530/351; 530/402; 930/144

(58) Field of Classification Search .................. None
See application file for complete search history.

(56) References Cited

U.S. PATENT DOCUMENTS

| 4,179,337 A | 12/1979 | Davis et al. ................. 435/181 |
| 4,609,546 A | 9/1986 | Hiratani ....................... 424/83 |
| 4,640,835 A | 2/1987 | Shimizu et al. ............... 424/94 |
| 5,264,209 A | 11/1993 | Mikayama et al. ......... 424/85.2 |
| 5,292,802 A | 3/1994 | Rhee et al. ................. 525/54.1 |
| 5,447,722 A | 9/1995 | Lang et al. ............... 424/280.1 |
| 5,468,478 A | 11/1995 | Saifer et al. .............. 424/78.27 |
| 5,677,171 A | 10/1997 | Hudziak et al. ........ 435/240.27 |
| 5,695,760 A | 12/1997 | Faanes et al. ............. 424/178.1 |
| 5,747,639 A * | 5/1998 | Seely .......................... 528/421 |
| 5,773,582 A | 6/1998 | Shin et al. ................... 530/351 |

FOREIGN PATENT DOCUMENTS

| EP | 0 372 752 A2 | 6/1990 |
| EP | 0 401 384 | 12/1990 |
| WO | WO 87/00056 A1 * | 1/1987 |
| WO | WO 94/05332 | 3/1994 |
| WO | WO 96/34015 | 10/1996 |
| WO | WO 97/32607 | 9/1997 |

OTHER PUBLICATIONS

Li et al. PEGylated recombinant human tumor necrosis factor alpha: preparation and anti-tumor potency. Acta Pharmacol Sin. Jun. 2001;22(6):549-55.*
Saifer et al. Plasma clearance and immunologic properties of long-acting superoxide dismutase prepared using 35,000 to 120,000 Dalton poly-ethylene glycol. Adv Exp Med Biol. 1994;366:377-87.*
Abuchowski, A. et al., "Effect of Covalent Attachment of Polyethylene Glycol on Immunogenicity and Circulating Life of Bovine Catalase", *J. Biol. Chem.*, 1977, 252(11), 3582-3586.
Bradford, M.M. et al., "A Rapid and Sensitive Method for the Quantitation of Microgram Auantities of Protein Utilizing the Principle of Protein-Dye Binding", *Anal. Biochem.*, 1976, 72, 248-254.
Carswell, E.A. et al., "An Endotoxin-induced Serum Factor that Causes Necrosis of Tumors", *J. Proc. Natl. Acad. Sci. USA*, 1975, 72(9), 3666-3670.
Habeeb, A.F.S.A., "Determination of Free Amino Groups in Proteins by Trinitrobenzenesulfonic Acid", *Anal. Biochem.*, 1966, 14, 328-339.
Monfardini, C. et al., "A Branched Monomethoxypoly (Ethylene Glycol) for Protein Modification", *Bioconjugate Chem.*, 1995, 6, 62-69.
Naoi, M. et al., "Alteration of the Substrate Specificity of *Aspergillus oryzae* β-Galactosidase by Modification with Polyethylene Glycol", *J. Appl. Biochem.*, 1984, 6, 92-102.
Pennica, D. et al., "Human Tumor Necrosis Factor: Precursor Structure, Expression and Homology to Lymphotoxin", *Nature*, 1981, 312, 724-729.
Pyatak, P.S. et al., "Preparation of a Polyethylene Glycol: Superoxide Dismutase Adduct, and an Examination of Its Blood Circulating Life and Anti-Inflammatory Activity", *Res. Comm. Chem. Pathol. Pharm.*, 1980, 29(1), 113-127.
Stocks, S.J., "A Flurometric Assay of the Degree of Modification of Protein Primary Amines with Polyethylene Glycol", *Anal Biochem.*, 1986, 154, 232-234.
Streekishma, K. et al., "High-Level Expression, Purification, and Characterization of Recombinant Human Tumor Necrosis Factor Synthesized in the Methylotrophic Yeast *Pichia pastoris*", *Biochem.*, 1989, 28, 4117-4125.
Tsutsumi, Y. et al., "Chemical Modification of Natural Human Tumor Necrosis Factor-α with Polyethylene Glycol Increases its Anti-Tumor Potency", *Jap. J. Cancer Res.*, 1994, 85, 9-12.
Tsutsumi, Y. et al., "Intravenous Administration of Polyethylene Glycol-Modified Tumor Necrosis Factor-α Completely Regresses Solid Tumor in Meth-A Murine Sarcoma Model", *Jap. J. Cancer Res.*, 1994, 85, 1185-1188.
Tsutsumi, Y. et al., "In vivo Anti-Tumor Efficacy of Polyehylene Glycol-Modified Tumor Necrosis Factor-α against Tumor Necrosis Factor-Resistant Tumors", *Jap. J. Cancer Res.*, 1997, 87, 1078-1085.
Zalipsky, S. et al., "Use of Functionalized Poly(Ethylene Glycol)s for Modification of Polypeptides", *Polyehtylene Glycol Chemistry: Biotechnical and Biomedical Applications*, Harris, J.M. (ed.), Plenum Press, New York, 1992, 21, 347-370.
Tsutsumi, Y. et al., "Molecular Design of Hybrid Tumor Necrosis Factor-α III: Polyethylene Gycol_Modified Tumor Necrosis Factor-αhas Markedly Enhanced Antitumor Potency due to Longer Plasma Half-Life and Higher Tumor Accumulation", *Journal of Pharmacalogy and Experimental Therapeutics, American Society for Pharmacalogy*, 1996, 278(3), 1006-1011.

(Continued)

*Primary Examiner*—David S Romeo
(74) *Attorney, Agent, or Firm*—Woodcock Washburn LLP

(57) ABSTRACT

Modifying TNF with polyethyleneglycol (PEG) having an approximate weight average molecular weight in the range of about 10,000 to about 40,000, preferably in the range of about 20,000 to 30,000, significantly increases the circulating half-life of the TNF while not increasing its toxicity. As a result, lower doses of the TNF may be administered to effectively treat tumors with fewer, accompanying adverse side effects to the patient.

20 Claims, 3 Drawing Sheets

OTHER PUBLICATIONS

Tsutsumi, Y. et al., "Molecular Design of Hybrid Tumor Necrosis Factor-α II: The Molecular Size of Polyethylene Glycol-Modified Tumour Necrosis Factor-Alpha Affects its Anti-tumour Potency", *Br J. Cancer*, 1996, 74(7), 1090-1095.

Mark, et al., "Site-Specific Mutagenesis to Modify the Human Tumor Necrosis Factor Gene", *Methods Enzymol*, 1987, 154, 403-414.

Tsutsumi, et al., "Molecular Design of Hybrid Tumour Necrosis Factor Alpha with Polyethylene Glycol Increases its Anti-tumour Potency", *Br. J. Cancer*, 1995, 71(5), 963-968.

Satake-Ishikawa, et al., "Chemical Modification of Recombinant Human Granulocyte Colony-Stimulating factor by Polyethylene Glycol Increases its Biological Activity in Vivo", *Cell Struct Funct.*, 1992, 17(3), 157-160.

Nakamura, et al., "A Novel Recombinant tumor Necrosis Factor-Alpha Mutant with increased Anti_tumor Activity and Lower Toxicity", *Int;. J. Cancer*, 1991, 48(5), 744-748.

\* cited by examiner

FIGURE 3

Sequence of the Secreated (mature) Mouse and Human TNF Protein (SEQ ID NO:1) Mouse  1 MSTESMIRDVELAEEALPQKMGGFQNSRRCLCLSLFSFLLVAGATTLFCLLNFGVIGPQR
(SEQ ID NO:2) Human  1 MSTESMIRDVELAEEALPKKTGGPQGSRRCLFLSLFSFLIVAGATTLFCLLHFGVIGPQR
                        **********
                        10

Mouse  61 DEKFPNGLPLISSMAQTL------------TLTNHQVEEQLEWLSQRANALLANGMDL
Human  61 EE-FPRDLSLISPLAQAVRSSSRTPSDKPVAHVVANPQAEGQLQWLNRRANALLANGVEL Mouse 107 KDNQLVVPADGLYLYLVYSQVLFKGQGCPD-YVLLTHTVSRFAISYQEKVNLLSAVKSPCPK
Human 120 RDNQLVVPSEGLYLIYSQVLFKGQGCPSTHVLLTHTISRIAVSYQTKVNLLSAIKSPCQR
                                                                      A
                                                                     166

Mouse 166 DTPEGAELKPWYEPIYLGGVFQLEKGDQLSAEVNLPKYLDFAESGQVYFGVIAL
Human 180 ETPEGAEAKPWYEPIYLGGVFQLEKGDRLSAEINRPDYLDFAESGQVYFGIIAL
              A                                A
             188                              204

MODIFIED TUMOR NECROSIS FACTOR

RELATED APPLICATIONS

This application is a divisional of U.S. patent application Ser. No. 09/504,280, filed Feb. 15, 2000, which is a continuation-in-part of U.S. patent application Ser. No. 09/006,810, filed Jan. 14, 1998, which claims the benefit of U.S. Provisional Patent Application Ser. No. 60/035,521, filed Jan. 15, 1997, each of which in incorporated herein in its entirety.

This invention is directed, inter alia, to tumor necrosis factor, and several mutant forms of tumor necrosis factor, formulated with polyethylene glycol having a molecular weight in the range of 10,000 to 40,000 and methods for treating tumors using such modified tumor necrosis factor.

BACKGROUND OF THE INVENTION

Malignant melanoma (stage 3) is a fatal disease killing most patients within one year of diagnosis. The incidence of melanoma is rapidly increasing in the United States and is even higher in other countries, such as Australia. Effective treatments for patients suffering from melanoma are urgently needed.

Kidney cancer currently kills approximately 13,000 individuals in the United States each year. This form of cancer is frequently not detected until it is well advanced. The only form of treatment that significantly affects a patient's prognosis is surgical resection of the affected organ. Unfortunately, because this type of cancer is highly metastatic, complete removal of all the metastasis is difficult, if not impossible.

Colon cancer is one of the most prevalent forms of cancer and currently kills approximately 140,000 individuals in the United States each year. Although there have been a large number of traditional chemotherapeutic drugs developed to treat this disease, long term survival (defined as the percentage of patients surviving five years or more) has not appreciably changed in the last four decades. Furthermore, all of the traditional chemotherapeutic drugs developed are highly toxic, have deleterious and often fatal side effects, and are expensive. A curative, non-toxic treatment for this disease is urgently needed.

A hallmark of melanomas, kidney and colon tumors is that these tumors quickly develop resistance to traditional chemotherapies. Even though patients may initially respond to chemotherapeutic treatment, drug-resistant tumors quickly arise and often kill the patient. An alternative way to treat these tumors would be to identify an "Achilles Heel" in the tumors and to develop therapies that would selectively treat that target. One such potential target has been identified. Specifically, it has been noted that all three of these types of tumors require extensive vascularization of each of the metastacies in order for the cancers to grow. Therefore, one would predict that a therapeutic agent which would inhibit the vascularization of these tumors may provide a unique means of treating these tumors.

Tumor necrosis factor (TNF) is a cytokine originally named for its ability to kill tumors. There are at least two different mechanisms by which TNF is believed to kill tumors. First is by a direct effect on the tumor itself. Second, TNF can selectively disrupt the vascularization of tumors, thus depriving the tumor of nutrients and oxygen and in so doing killing the tumor indirectly. This latter mechanism of killing was described in the first scientific publication describing TNF. Carswell and Old reported that the METH A tumor cells were completely resistant to TNF in vitro. *J. Proc. Natl. Acad. Sci USA*, 72:3666-3670 (1975). However, METH A tumors in mice were extremely sensitive to killing by TNF in vivo. It was later shown that TNF selectively disrupted the vascularization of these METH A tumors. Subsequently it was later shown that a factor (EMAP 2) is released by some tumors that renders the tumor vasculature susceptible to TNF killing. Thus, TNF can kill some tumors (such as METH A sarcomas) not by directly killing the tumor cells, but rather by killing the tumors' vasculature that provides the tumor with blood, oxygen and other nutrients necessary to live and grow.

Early clinical trials attempted to utilize TNF as a direct tumoricidal agent. This coupled with the fact that because TNF has a very short circulating half life (less than 20 minutes) in the circulation, extremely high doses of TNF were used which induced "shock"-like symptoms characterized by a precipitous drop in blood pressure and often death of the patient.

An alternative method of using TNF would be to formulate it so that it remains in the circulation longer thus giving it more time to react with (and thus destroy) the vasculature of the tumors. Several other therapeutic proteins which had very short circulating half lives have been formulated with polyethylene glycol (PEG) so that they circulate longer and remain in the vasculature. These proteins include asparaginase, adenosine deaminase, and super oxide dismutase. See, for example, Harras, J. M., in "Polyethylene Glycol Chemistry: Biotechnical and Biochemical Applications," Plenum Press (1992).

Relevant to the invention described here, a group of investigators in Japan (Tsutsumi et. al.) have described that TNF could be formulated with certain PEG and that the resulting material had substantially increased circulating half-life and greater anti-tumor activity. See, Tsutsumi, Y., et al., *Jap. J. Cancer Res.*, 85:9-12 (1994); Tsutsumi, Y., et al., *Jap. J. Cancer Res.*, 85:1185-1188 (1994); Tsutsumi, Y., et al., *Jap. J. Cancer Res.*, 87:1078-1085 (1997). However these investigators used only PEG with a molecular weight of 5000 (PEG5000) attached to the primary amines on TNF with a succinimidyl succinate linker and failed to determine not only the optimal method of attaching PEG to TNF but also the optimal attachment sites on the molecule.

SUMMARY OF THE INVENTION

It has now been found that TNF modified with polyethylene glycol (PEG) having an approximate weight average molecular weight much higher than that experimented with by Tsutsumi et al., namely, in the range of about 10,000 to about 40,000 and preferably in the range of about 20,000 to about 30,000, is a greatly and surprisingly enhanced tumoricidal agent.

For one thing, the PEG-modified TNF of this invention has a significantly longer circulating half life than the PEG5000-modified TNF of Tsutsumi et al. For example utilizing the technology discovered by Tsutsumi et al., the circulating half life of PEG-TNF was about 2 days. In contrast using the most preferred PEG-modified TNF described herein, the circulating half-life is greater than 16 days (an 8 fold increase).

The PEG-modified TNF of this invention also exhibits significantly and surprisingly enhanced tumoricidal activity compared to either native TNF or to TNF modifed as by Tsutsumi et al. For example, tests indicate that the anti-tumor ED50 of the most preferred embodiment of the invention (TNF modified by PEG-20000 through primary amine groups), is as little as 10-50 IU (0.01 ug), a 2000 fold improvement over the 1000-3000 IU (2 ug) ED50 for native TNF.

Also surprising is the discovery that the modified TNF of this invention, even though it is far more potent at curing tumors and circulates many times longer than native TNF, is actually much safer (and less toxic) to use than the TNF of Tsutsumi et al. Tests indicate that optimal formulation of PEG-TNF circulated 8 times longer, is 2000 fold more potent and about 500 fold less toxic than the PEG-TNF described by Tsutsumi et. al in their publications. Moreover, it has been shown that this optimal formulation methodology can be utilized with TNF of several species (mouse and human) and with both wild type TNF as well as several mutant TNF proteins. Thus the present invention has enormous versatility in being able to be applied to many different TNF molecules.

This invention, therefore, relates to the modified TNF, wherein TNF has been modified by covalently bonding to the TNF, either directly or through a biocompatible linking agent, and preferably through a primary amine on the protein, PEG molecules, each PEG molecule of has an approximate weight average molecular weight in the range of about 10,000 to about 40,000. Preferably, the TNF is modified with five to twelve of the PEG molecules, more preferably, with about five to nine PEG molecules.

This invention also relates to a method of treating a patient suffering from a tumor by administering to said patient a therapeutically effective amount of said modified TNF.

This invention further relates to a method of enhancing the circulating half life of TNF comprising modifying said TNF by covalently bonding to it, preferably through primary amines on the protein, between about five and twelve PEG molecules having an approximate weight average molecular weight in the range of about 10,000 to about 40,000.

This invention further relates to a method of enhancing the tumoricidal activity of TNF comprising modifying said TNF by covalently bonding to it, preferably through primary amines on the protein, between about five and twelve PEG molecules having an approximate weight average molecular weight in the range of about 10,000 to about 40,000.

This invention further relates to a method of enhancing the safety of TNF by covalently bonding to it, preferably through primary amines on the protein, five to twelve PEG molecules each molecule having a molecular weigh of 10,000 to 40,000.

DESCRIPTION OF THE DRAWINGS

FIG. 3 is the sequence of secreted (mature) mouse (SEQ ID NO:1) and human (SEQ ID NO:2) TNF. Position 1 is the N-terminus of the secreted TNF.

DETAILED DESCRIPTION OF THE INVENTION

Figure 1:
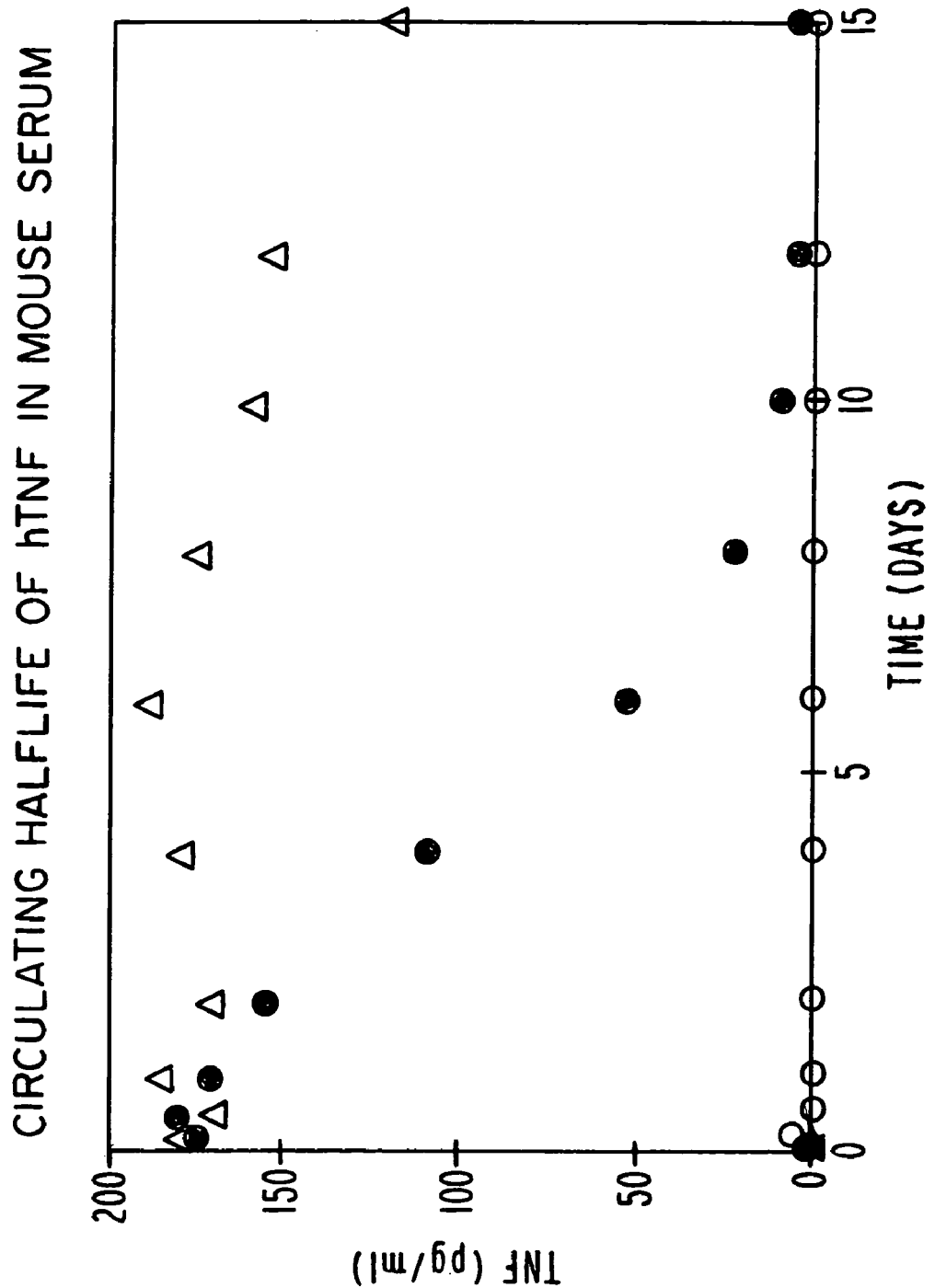
FIG. 1 is a graph depicting the circulating half life in mouse serum of native TNF (open circles), SS 5,000 MW PEG-TNF (closed circles), and 20,000 MW PEG-TNF (open triangles).

"Tumor necrosis factor" or "TNF" as used herein encompasses either naturally derived protein, such as isolated human or mouse TNF proteins, or protein produced using recombinant technology, such as recombinant murine TNF and recombinant human TNF or various TNF mutant proteins. Although the TNF-α protein is preferred, the term "TNF" also encompasses TNF-β protein. The terms also encompass TNF proteins that have been mutated by deletion or alteration of amino acids without significantly impairing biological activity. As non-limiting examples, such mutations include (reference being made to the sequence of the secreted protein, as illustrated in FIG. 3): the protein in which amino acids 1-9 (MSTESMIRD) (SEQ ID NO:3) of the human secreted protein are deleted; the protein in which lysine at position 166 is changed to alanine (SEQ ID NO:4): the protein in which lysine at positions 188 and 204 is changed to alanine (SEQ ID NO:5); and combinations of these mutations.

"Polyethylene glycol" or "PEG" refers to mixtures of condensation polymers of ethylene oxide and water, in a branched or straight chains, represented by the general formula $H(OCH_2CH_2)_nOH$. "Polyethylene glycol" or "PEG" is used in combination with a numeric suffix to indicate the approximate weight average molecular weight thereof of each molecule. For example, PEG 5,000 refers to polyethylene glycol having an approximate weight average molecular weight of about 5,000; PEG 12,000 refers to polyethylene glycol having an approximate weight average molecular weight of about 12,000; and PEG 20,000 refers to polyethylene glycol having an approximate weight average molecular weight of about 20,000. Such polyethylene glycols are available from several commercial sources, and are routinely referred to, as indicated above, by their weight average molecular weights.

"Melanoma" may be a malignant or benign tumor arising from the melanocytic system of the skin and other organs, including the oral cavity, esophagus, anal canal, vagina, leptomeningers, and/or the conjunctivae or eye. The term "melanoma" includes, for example, acral-lentginous melanoma, amelanotic melanoma, benign juvenile melanome, lentigo maligna melanoma, malignant melanoma, nodular melanoma, subungual melanoma and superficial spreading melanoma.

"Patient" refers to an animal, preferably a mammal, more preferably a human.

"Biocompatible" refers to materials or compounds which are generally not injurious to biological functions and which will not result in any degree of unacceptable toxicity, including allergenic and disease states.

"Circulating half life" refers to the period of time, after injection of the modified TNF into a patient, until a quantity of the TNF has been cleared to levels one half of the original peak serum level. Circulating half life may be determined in any relevant species, including humans or mice.

"Covalently bound" as used herein refers to a covalent bond linking the TNF protein to the PEG molecule, either directly or through a linker.

According to this invention, TNF is modified with polyethylene glycol having an approximate weight average molecular weight in the range of 10,000 to 40,000, preferably in the range of 20,000 to 30,000. Generally, polyethylene glycol with a molecular weight of 30,000 or more is difficult to dissolve, and yields of the formulated product are greatly reduced. The polyethylene glycol may be branched or straight chain, but is preferably a straight chain.

The polyethylene glycols may be bonded to the TNF through biocompatible linking groups. As discussed above, "biocompatible" indicates that the compound or group is non-toxic and may be utilized in vitro or in vivo without causing injury, sickness, disease or death. PEG may be bonded to the linking group, for example, via an ether bond, an ester bond, a thiol bond, or an amide bond. Suitable biocompatible linking groups include, for example, an ester group, an amide group, an imide group, a carbamate group, a carboxyl group, a hydroxyl group, a carbohydrate, a maleimide group (including, for example, succinimidyl succinate (SS), succinimidyl propionate (SPA), succinimidyl carboxymethylate (SCM), succinimidyl succinamide (SSA), or N-hydroxysuccinimidyl (NHS), an epoxide group, an oxycarbonylimidazole group (including, for example, nitrophenyl carbonate (NPC) or trichlorophenyl carbonate (TPC)), a trysylate group, an aldehyde group, an isocyante group, a vinylsulfone group, a tyrosine group, a cysteine group, a histidine group or a primary amine. Preferably, the biocompatible linking group is an ester group and/or a maleimide group and bonds to the TNF through a primary amine on the TNF protein. More preferably, the linking group is SS, SPA, SCM, SSA or NHS; with SS being the most preferred.

Alternatively, TNF may be coupled directly to PEG (i.e., without a linking group) through an amino group, a sulfhydryl group, a hydroxyl group, or a carboxyl group.

Methods for covalently bonding TNF to PEG, directly or via a biocompatible linking group, are known in the art, as described, for example, in Harras, J. M., in "Polyethylene Glycol Chemistry: Biotechnical and Biochemical Applications," Plenum Press (1992), the disclosure of which is herein incorporated by reference. It is preferred that the TNF protein be covalently bonded to five to twelve PEG molecules. Methods for determining the number of PEG molecules bonded to the protein are known in the art, for example, Habeeb, A. F. S. A., *Anal. Biochem.*, 14:328-339 (1966); Harras, J.M., supra., herein incorporated by reference. The number of PEG molecules bonded to TNF will vary according to the linking group utilized, the length of reaction, and the molar ratios of TNF and PEG utilized in the reaction.

As one skilled in the art would recognize, the modified TNF of this invention may be administered in a number of ways, for example, orally, intranasally, intraperitoneally, parenterally, intravenously, intralymphatically, intratumorly, intramuscularly, interstitially, intrarterially, subcutaneously, intraocularly, intrasynoially, transepithelially, and transdermally. A therapeutically effective amount of one of the modified compounds of the present invention is an amount effective to inhibit tumor growth, and that amount may vary according to the method of administration. Generally, effective doses should be in the range of about 0.001 to 0.1 mg/kg, once a week. The modified TNF may be formulated with pharmaceutically acceptable carriers and diluents, as known in the art. For example, for intravenous? administration, the modified TNF may be mixed with a phosphate buffered saline solution, or any other appropriate solution known to those skilled in the art, prior to injection. Tests have shown that the modified TNF is particularly effective in treating melanoma, colon cancer, kidney cancer and breast cancer tumors.

The invention is further demonstrated in the following examples, which are for purposes of illustration, and are not intended to limit the scope of the present invention.

TNF used in the experiments described below was of mouse TNF and human TNF or human TNF mutants. The human TNF was produced in *E. coli* and *Pichea pasatoris*, and murine TNF as well as the human TNF mutants were produced in *Pichea pastoris*. Recombinant TNF was produced in *E. coli* or *Pichea* using methods similar to those described in Pennica, D., et al., *Nature,* 312:724-729 (1981); Streekishna, K., et al., *Biochemistry,* 28:4117-4125 (1989). The mouse TNF was produced in *E. coli* and in *Pichea*.

EXAMPLE 1

Attachment of PEG to TNF

Coupling PEG to TNF was performed using the general methods described in Harras, J. M., cited above. To TNF (1 mg/ml in 100 mm phosphate buffer, pH 7.2-7.5), the SS-PEG, SP-PEG or NHS-PEG was added at a 10 to 50 molar excess and mixed for one hour at room temperature. This results in approximately 8-12 PEG molecules being attached to the primary amines of each molecule of TNF. Other PEG linkers and attachment sites required different pH, reaction times and amounts of PEG all of which must be empirically determined. All PEG-TNF formulations were purified by removing unreacted PEG and from the PEG-TNF by ultra filtration using a 100 kDa cut off filter. In each of the modifications referenced in this example, the TNF was modified with five to 15 molecules of PEG.

Purity of the PEG-TNF was assessed by SDS-PAGE and the percent of primary amines modified by this procedure was determined using florescamine as described by S. J. Stocks (Anal. Biochem. 154:232 (1986)). SDS-PAGE results indicated that very little, if any, native TNF remained in the preparation after pegylation.

EXAMPLE 2

Specific Activity of TNF

Prior to pegylation (native TNF), both human and mouse was tested for its biological activity using the L929 cytotoxicity assay originally described in the first publication on TNF and in detail below. The specific activity of the TNF was $10^6$ I.U. units per milligram. The protein concentration was determined by the method of Bradford. Bradford, M. M., *Anal. Biochem.,* 72:248-254 (1976). BSA was used as a standard. Purity of the preparation was assessed by SDS-PAGE gel. All preparations used were >99% pure (i.e. less than 1% of native TNF remained in the PEG-TNF.

EXAMPLE 3

L-929 Cytotoxicity Testing of PEG-TNF

The PEG-TNF were examined for in vitro cytotoxic activity using the L-929 cytotoxicity assay performed according to the procedure set forth below. The specific activity of the native TNF starting material was $1.5 \times 10^6$ units/mg a value. The specific activity of the PEG-TNF was most often less than one half of the specific activity of the native TNF. This experiment was repeated using a wide variety of PEG molecular weights, methods of attachment (linkers) and sites of attachment (see Table 1).

TABLE 1

Effects of The Attachment Site, Linker Chemistry and PEG molecular Weight on the Biological Activity of TNF measured In Vitro (L-929 Cytotoxicity of PEG-TNF)

| Attachment Site | Linker | Molecular Weight of PEG | % Activity Retained |
|---|---|---|---|
| Primary Amines | SS-PEG | 5,000 mw | 55 |
| | SS-PEG | 12,000 mw | 53 |
| | SS-PEG | 20,000 mw | 56 |
| | SS-PEG | 30,000 mw | 54 |
| | SS-PEG | 40,000 mw | 55 |
| | SP-PEG | 5,000 mw | 51 |
| | SP-PEG | 20,000 mw | 52 |
| | PEG2-NHS | 10,000 mw | 49 |
| | PEG2-NHS | 20,000 mw | 52 |
| | PEG2-NHS | 40,000 mw | 54 |
| Hydroxyl groups | Epoxy PEG | 5,000 mw | 38 |
| | Epoxy PEG | 8,000 mw | 38 |
| | Glycedal ether | 5,000 mw | 0 |

TABLE 1-continued

Effects of The Attachment Site, Linker Chemistry and
PEG molecular Weight on the Biological Activity of TNF
measured In Vitro (L-929 Cytotoxicity of PEG-TNF)

| Attachment Site | Linker | Molecular Weight of PEG | % Activity Retained |
|---|---|---|---|
| Carboxyl groups | Nitro Phenyl | 5,000 mw | 21 |
| | Trichloro Phenyl | 5,000 mw | 11 |
| | Tresylate | 5,000 mw | 8 |
| | PEG aldehyde | 5,000 mw | 0 |
| Sulfhydral groups | Vinyl sulfone | 5,000 mw | 12 |
| | Isocynate | 5,000 mw | 19 |
| | Maleimide | 5,000 mw | 43 |

EXAMPLE 4

Determination of Serum Half Life of PEG-TNF

In order to measure the circulating half life (serum half life) of TNF and PEG-TNF, an ELISA assay for human and mouse TNF obtained from Genzyme was used. The kit was used as suggested by the manufacturer. Mice were injected with either TNF or PEG (100 units) i.p., and approximately 25 μl of serum was collected from retro-orbital bleeds at the times indicated in FIG. 1. A total of 5 mice (female, C57 bl6 mice, 20-25 g) were in each group.

The native TNF (open circles) was cleared very fast, and the only data point above baseline was 30 minutes post-injection.

The SS 5,000 MW peg-TNF (closed circles) had a half life of about 4 days. The half life of the 20,000 MW PEG-TNF (open triangles) was >15 days.

Figure 2:
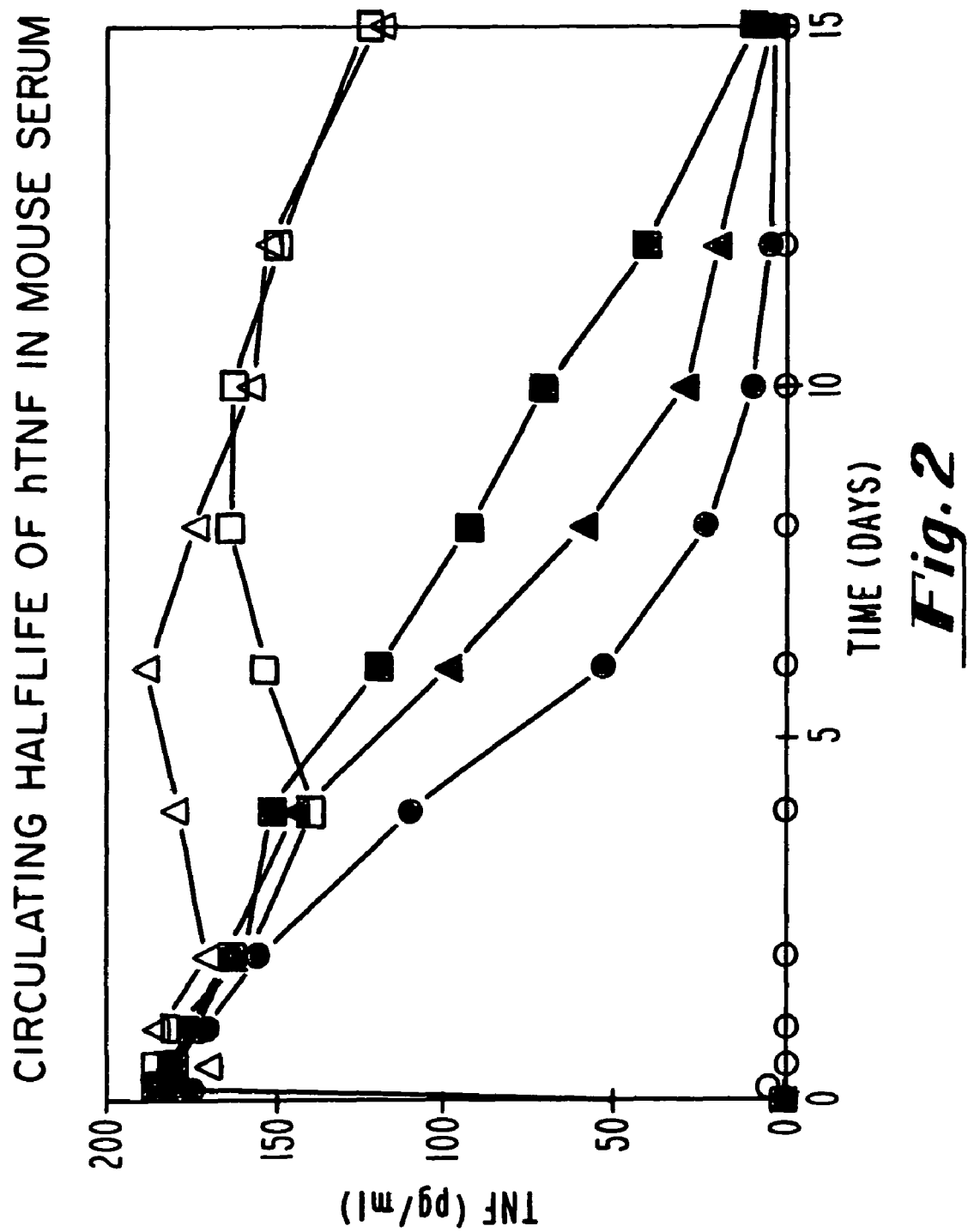
FIG. 2 is a graph depicting the circulating half life in mouse serum of native TNF (open circles), SS 5,000 MW PEG-TNF (closed circles), SS 12,000 MW PEG-TNF (closed triangles), SS-20,000 MW PEG-TNF (open triangles), NHS 12,000 MW PEG-TNF (closed squares), and NHS 20,000 MW PEG-TNF (open squares).

This experiment was repeated using the treatment groups listed below, and the results presented in FIG. 2: native TNF (open circles); SS 5,000 MW PEG-TNF-α (closed triangles); SS 20,000 MW PEG-TNF (open triangles); NHS 12,000 MW PEG-TNF-α (closed squares). The serum half life for the different treatment groups was >15 days for NHS 20,000 MW PEG-TNF and SS 20,000 MW PEG-TNF-α; approximately 4 days for SS 5,000 MW PEG-TNF; approximately 6 days for SS 12,000 MW PEG-TNF; approximately 8 days for NHS 12,000 MW PEG-TNF; and 30 min post-injection for native TNF. In summary, each PEG-TNF exhibited a much longer half life than native TNF; however, the NHS 20,000 MW PEG-TNF and the SS 20,000 MW PEG-TNF had significantly longer half lives (>15 days) than the TNF modified with lower molecular weight PEG.

Data from these and other experiments performed with additional PEGs, linkers and sites of attachment are shown in Table 2.

TABLE 2

Effects of The Attachment Site, Linker Chemistry
and PEG molecular Weight on Circulating Half Life
and In Vitro Cytotoxicity Using L-929 Cells Serum Half-Life = 0.02 days (~20 minutes)

| Native Human TNF Attachment Site | Linker | Molecular Weight of PEG | Serum Half-Life (days) |
|---|---|---|---|
| Primary Amines | SS-PEG | 5,000 mw | 4 |
| | SS-PEG | 12,000 mw | 8 |
| | SS-PEG | 20,000 mw | 16 |
| | SS-PEG | 30,000 mw | 17 |
| | SS-PEG | 40,000 mw | 17 |
| | SP-PEG | 5,000 mw | 5 |
| | SP-PEG | 20,000 mw | 8 |
| | PEG2-NHS | 10,000 mw | 7 |
| | PEG2-NHS | 20,000 mw | 16 |
| | PEG2-NHS | 40,000 mw | 18 |
| Hydroxyl groups | Epoxy PEG | 5,000 mw | 5 |
| | Epoxy PEG | 8,000 mw | 6 |
| | Glycedal ether | 5,000 mw | 12 |
| Carboxyl groups | Nitro Phenyl | 5,000 mw | 5 |
| | Trichloro Phenyl | 5,000 mw | 5 |
| | PEG aldehyde | 5,000 mw | 21 |
| Sulfhydral groups | Vinyl sulfone | 5,000 mw | 3 |
| | Isocynate | 5,000 mw | 3 |
| | Maleimide | 5,000 mw | 2 |

These experiments illustrate that by attaching PEG to the primary amines and using PEG of 20,000 to 30,000 mw, the optimum retention of biological activity measured in vitro (L-929 cytoxicity) and the longest circulating half life in vivo are observed. However, a remaining concern is whether increasing the circulating half life of the PEG-TNF would greatly increase the toxicity of the TNF.

EXAMPLE 5

Lethality of the PEG-TNF

As a screen, two C57 bl6 mice (female, 20-25 g) were injected intraperitoneally (i.p.) with either native TNF or SS-PEG-TNF and survival of the animals was monitored. The doses used were 1, 5, and 10 thousand units of activity.

With native TNF, the following results were obtained:

10,000 I.U.—both mice dead the next morning 5,000 I.U.—one mouse dead next morning; the second mouse in obvious distress (hair ruffled and little movement) and dead after 2 days 1,000 I.U.—one mouse dead the next morning; the second mouse in distress (hair ruffled and little movement) and in such poor condition after 2 days that it was euthanized With the SS-PEG-TNF, all mice at all doses remained in good health for two weeks following injection. Behavior was normal, as was eating and drinking. There was no change in coat (fur was not ruffled). All of the mice were euthanized 15 days post-injection.

TNF kills mice by causing an abrupt drop in blood pressure. Blood pressure in mice can be measured using a pressure cuff around the tail, much as blood pressure is measured using a pressure cuff around the arm of a human. Because it has been shown that TNF is more lethal to mice having tumors, than normal mice, the animals used in this experiment were implanted with METH A sarcomas grown to approximately 0.5 cm in diameter. In these experiments we injected mice (5 in each group) with various amounts of TNF or PEG-TNF and the blood pressure was measured 2 hours post treatment (the time of minimum blood pressure following treatment. In Table 3 below, the hypotension ED50 is the amount of TNF or modified TNF that caused 50% of the mice to experience hypotension or shock.

High doses of TNF can kill mice within 2 days following treatment. The amount of TNF required to kill half of the mice is calculated at the $LD_{50}$ (Lethal Dose that kills 50% of the mice). Long Term survival is affected by tumor growth and thus an effective Anti-Tumor dose of TNF Is defined as the lowest dose required to enable a treated mouse to live twice as long as a mouse that does not receive treatment. The amount of TNF or PEG-TNF required to double the life expectancy (by killing the tumor) of 50% of the animals is presented as the Anti-Tumor Activity $ED_{50}$ in Table 3. All amounts of TNF are expressed as the amount of TNF protein and dose not include the weight of the PEG.

An ideal formulation of TNF would result in a PEG-TNF that exhibiting a high LD50 (be less lethal), a high $ED_{50}$ for blood pressure decrease (not cause hypotension or shock), and a low $ED_{50}$ for Anti-Tumor Activity (that is, be very potent at killing the tumor).

In this experiment, succimimidyl succinamide (SS) linker was used to link PEG 20,000 to the primary amines of mouse, human and several biologically active TNF mutants, to see if this formulation technology could be applied to other forms of TNF. The results from these experiments are summarized in Table 3 below

TABLE 3

How does Formulation With PEG Effect TNF Toxicity and Anti-Tumor Activity

| Species of TNF | Formulation | $LD_{50}$ | Hypo-tension ($ED_{50}$) | Anti-Tumor Activity ($ED_{50}$) |
|---|---|---|---|---|
| Murine | Native TNF | 2 ug | 1 ug | 20 ug |
|  | PEG TNF | 100 ug | 2 ug | 0.01 ug |
| Human | Native TNF | 7 ug | 1 ug | 60 ug |
|  | PEG TNF | 300 ug | 4 ug | 0.005 ug |
| Human -77-87 | Native TNF | 60 ug | 1 ug | 2 ug |
|  | PEG TNF | 100 ug | 5 ug | 0.002 ug |
| Human 188, 204 K-A | Native TNF | 300 ug | 100 ug | 2 ug |
|  | PEG TNF | 300 ug | 100 ug | 20 ug |

EXAMPLE 6

Antitumor Activity of PEG-TNF

The results presented above indicate that modification of TNF with PEG according to this invention not only reduces the lethality of the TNF, but that especially the TNF modified with PEG having a molecular weight of approximately 20,000 exhibited a surprisingly enhanced circulating half life and surprisingly and significantly enhanced anti-tumor activity.

To test the anti tumor activity of the 20,000 mw PEG-TNF with that of the native TNF and the PEG-TNF described by Tsutsumi et al., a test was carried out utilizing the B16 murine melanoma model. C57 bl6 female mice (20-25 g) were injected with one million B16 melanoma cells, s.q. on flank. The tumors were allowed to grow for one week prior to treatment. There were 5 mice in each treatment group, and animals were treated once a week for three weeks. The number of days the animals survived was noted ( the experiment was terminated at 180 days and all animals were euthanized; however the animals that survived this amount of time were all tumor free and in good health), and the results are shown below in Table 4.

TABLE 4

Effect of Native TNF and PEG-TNF on Survival of Mice Implanted with B16 Melanomas

| Treatment Group | Survival Time (days) | Average Survival Time |
|---|---|---|
| Saline control | 18, 18, 20, 21, 24 | 20.2 days |
| Native TNF |  |  |
| 10 IU | 17, 18, 19, 21, 21 | 20.2 days |
| 100 IU | 16, 18, 19, 19, 23 | 19.0 days |
| SS-PEG 5,000 mw TNF |  |  |
| 10 IU | 20, 22, 24, 26, 27 | 23.6 days |
| 100 IU | 21, 22, 24, 26, 27 | 25.0 days |
| 1000 IU | 21, 49, 53, 180, 180 | 96.6 days |
| SS-PEG 20,000 mw TNF |  |  |
| 10 IU | 38, 180, 180, 180, 180 | 96.6 days |
| 100 IU | 180, 180, 180, 180, 180 | 180 days |
| 1000 IU | 180, 180, 180, 180, 180 | 180 days |

Note that all animals surviving 180 days were devoid of tumors and were euthanized.

Similar experiments were performed using a variety of other tumors including kidney, colon leukemia and breast cancer. Mice were injected with $1 \times 10^6$ tumor cells and, two weeks later, were injected i.p. with the 20,000 mw PEG-TNF once a week, for three weeks. Cure was defined as the percent of animals surviving five times longer than untreated animals. Results are presented in Table 5 and indicate that the modified TNF of this invention is effective in treating melanoma tumors, kidney tumors, colon tumors, and breast tumors.

TABLE 5

Identification of tumors most sensitive to TNF

| Tumor Type | Cell Line | Dose of PEG-TNF | % cured |
|---|---|---|---|
| Kidney | G401 | 10 IU | 80 |
|  |  | 30 IU | 80 |
| Colon | HT29 | 10 IU | 40 |
|  |  | 30 IU | 60 |
|  |  | 100 IU | 80 |
| Breast | MCF7 | 10 IU | 0 |
|  |  | 30 IU | 0 |
|  |  | 100 IU | 20 |
| Brain | SW1088 | 100 IU | 0 |
| Leukemia | L1210 | 100 IU | 0 |
| Hepatoma | Hep3B | 100 IU | 0 |

The results presented above are surprising for a number of reasons. First, there was no way to predict that modifying TNF with high molecular weight PEG would increase the circulating half-life of the TNF. Indeed, the clearance rate of proteins in general cannot be predicted based on their molecular weight. Second, although it had been previously shown that proteins modified with PEG circulate longer than proteins without PEG, it had not, to the inventor's knowledge, ever been shown or suggested that simply increasing the molecular weight of the PEG would can have a dramatic effect on the circulating half-life of the PEG protein. Third, it had not been previously shown or suggested that using 20,000-30,000 molecular weights of PEG would provide the optimal circulating half life. Fourth, it was unexpected that modification of TNF with high molecular weight PEG, although it decreases the in vivo activity of TNF in killing L-929 cells, would actually enhance the tumoricidal activity of the TNF in vivo. This is particularly surprising in view of the added stearic hindrance expected to be created by the high molecular weight modifier such that it would be unable to interact with TNF receptors. Finally, although one would have predicted that the modified TNF, because of its enhanced circulating half life, would have been even more toxic than the native TNF, this, surprisingly, was not the case.

Table 6, below, provides a comparison of the activity, half life, lethality and anti-tumor activity for native TNF, for PEG5000-modified TNF, as disclosed by Tstusumi et al., and for the preferred embodiment of this invention, PEG20,000-modified TNF.

TABLE 6

Comparison of the Activities and Toxicities of Various PEG and Native TNF

|  | Native TNF | Tsutsumi's PEG-TNF | 20,000 mw PEG-TNF |
|---|---|---|---|
| In vitro activity (L-929 Cell cytotoxicity) | 100% | 56% | 54-56% |
| Circulating half life | 20 min | 3-5 hours | 16-18 days |
| Lethality in Tumor free mice ($LD_{50}$) | 20-70 ug | ND | 300 ug |
| Mice with METH A tumors | 1-2 ug | 10 ug | 300 ug |
| Dose required to cure 50% of mice with tumors | | | |
| METH A sarcoma | >2 ug | 10 ug | 0.01 ug |
| B16 Melanoma | >2 ug | 10 ug | 0.01 ug |

METHODS AND MATERIALS

In Vitro Cytotoxicity Assay
  Materials
  L929 fibroblasts ATCC #CCL1 NCTC clone 929.
  Dulbecco's Modified Essential Medium (DMEM) and Fetal Bovine
  Serum (GIBCO Laboratories, Grand Island, N.Y. #16000-010)
  Recombinant Human Tumor Necrosis Factor-α (TNF-α) (prepared in-house)
  Microtiter Plate Reader (Molecular Devices Corp., Menlo Park, Calif., Emax)
  Method B. Propagation of L929 Fibroblasts:
  Cells were grown in DMEM supplemented with 10% Fetal Bovine Serum Incubate overnight in a 37° C., 5% $CO_2$ humidified incubator. Cells were planted in a 96 well plates (3,000 cells/well in 0.15 ml of DMEM containing Fetal Bovine Serum. After 24 hours of growth, TNF or PEG TNF was added to the wells and the plates were incubated an additional 24 hours the viability of the cells was determined by adding 20 µl of 3[4,5-dimethylthiazol-2-yl]-2,5-diphenyltetrazolium bromide (MTT) (25 mg/ml in phosphate buffered saline pH 7.4) to each well of the culture plate and incubating the cultures at 37° C. for four hours. After that time, the culture supernatents were discarded and 150 µl of DMSO was added to each well. The absorbance of each well at 570 nm was determined using a micro titer plate reader. Wells that exhibit an $A_{540}$ closest to 50% of the arithmetic mean of the control are considered to represent 50% lysis (1 unit) of the L929 cells.

Determination of Circulating Half Life of PEG-TNF
  Materials
  ELISA Kits from Genzyme (Cambridge, Mass.),
  Methods
  The Elisa kits were used as suggested by the manufacturer. Serum samples were collected from retro orbital plexus using heparinized 50 µl capillary tubes. A pretreatment blood sample was collected just prior to i.v. injection with TNF or PEG-TNF formulations. Additional blood samples were collected at 30 minutes, 24 hours as well as 3, 7, 12 and 15 days post-treatment. The samples were centrifuged and the resulting supernatant was stored frozen at −20° C. until being assayed.

What is claimed is:

1. A method of enhancing the tumoricidal activity of isolated TNF comprising covalently bonding to the TNF PEG having an approximate weight average molecular weight in the range of 20,000 to 40,000.

2. The method of claim 1 wherein the PEG is covalently bound to primary amine groups on the TNF through a biocompatible linker.

3. The method of claim 2 wherein the biocompatible linker is succinimidyl succinate, succinimidyl proprionate, or N-hydroxy succinimidyl.

4. The method of claim 1 wherein the PEG has an approximate weight average molecular weight in the range of 20,000 to 30,000.

5. The method of claim 1 wherein the TNF is TNF-α.

6. The method of claim 1 wherein the TNF is isolated human TNF.

7. The method of claim 1 wherein the TNF is recombinant human TNF.

8. The method of claim 1 wherein the TNF is human TNF mutated by deleting amino acids 1 to 9 of the mature TNF protein.

9. A method of inhibiting tumor growth in a patient suffering from cancer comprising administering to the patient a therapeutically effective amount of isolated TNF covalently bound to PEG having an approximate weight average molecular weight in the range of 20,000 to 40,000.

10. The method of claim 9 wherein the tumor is a melanoma.

11. The method of claim 9 wherein the tumor is a colon cancer.

12. The method of claim 9 wherein the tumor is a kidney cancer.

13. The method of claim 9 wherein the tumor is a breast cancer.

14. The method of claim 9 wherein the PEG is covalently bound to primary amine groups on the TNF through a biocompatible linker.

15. The method of claim 14 wherein the biocompatible linker is succinimidyl succinate, succinimidyl proprionate, or N-hydroxy succinimidyl.

16. The method of claim 9 wherein the PEG has an approximate weight average molecular weight in the range of 20,000 to 30,000.

17. The method of claim 9 wherein the TNF is TNF-α.

18. The method of claim 9 wherein the TNF is isolated human TNF.

19. The method of claim 9 wherein the TNF is recombinant human TNF.

20. The method of claim 9 wherein the TNF is human TNF mutated by deleting amino acids 1 to 9 of the mature TNF protein.

* * * * *

SEQUENCE LISTING

<160> NUMBER OF SEQ ID NOS: 5

<210> SEQ ID NO 1
<211> LENGTH: 219
<212> TYPE: PRT
<213> ORGANISM: Mouse

<400> SEQUENCE: 1

```
Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
            20                  25                  30

Leu Ser Leu Phe Ser Phe Leu Leu Val Ala Gly Ala Thr Thr Leu Phe
        35                  40                  45

Cys Leu Leu Asn Phe Gly Val Ile Gly Pro Gln Arg Asp Glu Lys Phe
    50                  55                  60

Pro Asn Gly Leu Pro Leu Ile Ser Ser Met Ala Gln Thr Leu Thr Leu
65                  70                  75                  80

Thr Asn His Gln Val Glu Glu Gln Leu Glu Trp Leu Ser Gln Arg Ala
                85                  90                  95

Asn Ala Leu Leu Ala Asn Gly Met Asp Leu Lys Asp Asn Gln Leu Val
```

```
                100                 105                 110
Val Pro Ala Asp Gly Leu Tyr Leu Val Tyr Ser Gln Val Leu Phe Lys
            115                 120                 125

Gly Gln Gly Cys Pro Asp Tyr Val Leu Leu Thr His Thr Val Ser Arg
        130                 135                 140

Phe Ala Ile Ser Tyr Gln Glu Lys Val Asn Leu Leu Ser Ala Val Lys
145                 150                 155                 160

Ser Pro Cys Pro Lys Asp Thr Pro Glu Gly Ala Glu Leu Lys Pro Trp
                165                 170                 175

Tyr Glu Pro Ile Tyr Leu Gly Gly Val Phe Gln Leu Glu Lys Gly Asp
            180                 185                 190

Gln Leu Ser Ala Glu Val Asn Leu Pro Lys Tyr Leu Asp Phe Ala Glu
        195                 200                 205

Ser Gly Gln Val Tyr Phe Gly Val Ile Ala Leu
        210                 215

<210> SEQ ID NO 2
<211> LENGTH: 233
<212> TYPE: PRT
<213> ORGANISM: Homo sapiens

<400> SEQUENCE: 2

Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
        50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 3
<211> LENGTH: 9
```

```
<212> TYPE: PRT
<213> ORGANISM: Homo sapiens

<400> SEQUENCE: 3

Met Ser Thr Glu Ser Met Ile Arg Asp
1               5

<210> SEQ ID NO 4
<211> LENGTH: 233
<212> TYPE: PRT
<213> ORGANISM: Homo sapiens

<400> SEQUENCE: 4

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Ala Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 5
<211> LENGTH: 233
<212> TYPE: PRT
<213> ORGANISM: Homo sapiens

<400> SEQUENCE: 5

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
```

-continued

```
                50                       55                       60
Arg Asp Leu Ser Leu Ile Ser Pro Leu Ala Gln Ala Val Arg Ser Ser
65              70                  75                  80

Ser Arg Thr Pro Ser Asp Lys Pro Val Ala His Val Val Ala Asn Pro
            85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Ala Pro Trp Tyr Glu
            180                 185                 190

Pro Ile Tyr Leu Gly Gly Val Phe Gln Leu Glu Ala Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230
```